(12) United States Patent
Infanger et al.

(10) Patent No.: US 11,052,201 B2
(45) Date of Patent: Jul. 6, 2021

(54) PROTECTIVE COVER FOR A DENTAL SYRINGE NEEDLE

(71) Applicant: Verena Solutions LLC, Chicago, IL (US)

(72) Inventors: Michael Infanger, Park Ridge, IL (US); Michael A. Carvajal, Chicago, IL (US)

(73) Assignee: Verena Solutions LLC, Chicago, IL (US)

( * ) Notice: Subject to any disclaimer, the term of this patent is extended or adjusted under 35 U.S.C. 154(b) by 51 days.

(21) Appl. No.: 16/222,471

(22) Filed: Dec. 17, 2018

(65) Prior Publication Data

US 2020/0188604 A1 Jun. 18, 2020

(51) Int. Cl.
*A61M 5/32* (2006.01)

(52) U.S. Cl.
CPC ........ *A61M 5/3202* (2013.01); *A61M 5/3293* (2013.01); *A61M 2202/048* (2013.01); *A61M 2205/581* (2013.01); *A61M 2210/0625* (2013.01)

(58) Field of Classification Search
CPC .............. A61M 5/3271; A61M 5/3272; A61M 5/3243; A61M 2005/3247; A61M 2005/3253; A61M 2005/3109; A61M 2005/3206; A61M 5/347; A61M 2205/581; A61M 5/3202; A61M 5/002; A61M 5/3254
See application file for complete search history.

(56) References Cited

U.S. PATENT DOCUMENTS

| | | |
|---|---|---|
| 3,605,744 A | 9/1971 | Dwyer |
| 3,820,652 A | 6/1974 | Thackston |
| 4,425,120 A | 1/1984 | Sampson et al. |
| 4,917,669 A | 4/1990 | Bonaldo |
| 4,943,282 A | 7/1990 | Page et al. |
| 4,994,045 A | 2/1991 | Ranford |
| 5,112,307 A | 5/1992 | Haber et al. |
| 5,137,524 A | 8/1992 | Lynn et al. |
| 5,222,502 A | 6/1993 | Kurose |
| 5,232,457 A | 8/1993 | Grim |
| 5,405,326 A | 4/1995 | Haber et al. |
| 5,891,104 A | 4/1999 | Shonfeld et al. |
| 6,485,469 B1 | 11/2002 | Stewart et al. |
| 6,764,465 B2 | 7/2004 | Chen |
| 8,721,546 B2 | 5/2014 | Belson |
| 9,682,196 B1 * | 6/2017 | Infanger .............. A61M 5/3204 |
| 10,342,930 B1 | 7/2019 | Infanger et al. |
| 2003/0014018 A1 * | 1/2003 | Giambattista ......... A61M 5/002 604/198 |
| 2005/0038399 A1 | 2/2005 | Suzuki et al. |
| 2005/0245875 A1 | 11/2005 | Restelli et al. |

(Continued)

*Primary Examiner* — Emily L Schmidt
(74) *Attorney, Agent, or Firm* — Andrus Intellectual Property Law, LLP

(57) ABSTRACT

A protective dental needle includes a sheath having a cylindrical body with a channel along the cylindrical body. A needle assembly includes a hypodermic needle extending through a hub. The needle assembly is retained within the sheath and movable within the sheath between a retracted position and an extended position. A needle cap is positioned external to the sheath. The needle cap includes a plurality of longitudinal ribs that extend from an interior surface of the needle cap.

17 Claims, 8 Drawing Sheets

(56) References Cited

U.S. PATENT DOCUMENTS

2006/0282044 A1    12/2006  Mohammed
2007/0156101 A1*    7/2007  Liversidge ............ A61M 5/002
                                                          604/218
2017/0021110 A1*    1/2017  Srinivasan ............ A61M 5/002
2017/0143912 A1*    5/2017  Hu ...................... A61M 5/3202

* cited by examiner

PROTECTIVE COVER FOR A DENTAL SYRINGE NEEDLE

BACKGROUND

The present disclosure relates generally to dental syringes and more specifically to a protective cover for a dental syringe needle, which reduces the risk of injury due to accidental needle pricks.

Localized anesthesia minimizes the pain felt by the patient and may make the patient more compliant to receive medical treatment. While the patient is under the effects of anesthesia, the medical professional has more freedom to operate about the patient, resulting in a faster procedure.

The syringes used to administer local anesthetics use a disposable cartridge of local anesthetic and a disposable needle, which attaches to an end of the syringe. The disposable needle is supplied by the manufacturer with a two part protective cover. The back part of the cover fits over the mounting hub of the needle and extends one centimeter past a back end of the front cover and is removed when the syringe is loaded for use. The front portion remains as a protective cover to preserve the sterility of the needle and to protect a user, while handling the syringe prior to and after use. The front portion of the protective cover is referred to as a "needle cap," because of the manner in which the back portion of the cover telescopes over the front portion and the two are sealed together, an annular ridge or shoulder is created one centimeter from the back end of the front portion of the cap. All commercially available needles for dental office use at this time have a similar ridge or shoulder as the apparatus used to attach the needle to most dental syringes is the same. The needles and their protective needle caps intended for use in dental offices are supplied in different lengths for use in Mandibular and Maxillary injections. The Mandibular needle cap is 4.5 to 5 centimeters long from the previously mentioned shoulder to the front end and the Maxillary needle cap is 3 to 3.5 centimeters long between those points. The diameter of the cap at the shoulder is 1 centimeter and immediately behind the shoulder the diameter is less, usually 0.85 centimeters.

The needle cap is removed immediately prior to administering the injection to the patient. The danger of an infectious needle stick occurs when the protective needle cap is replaced on the needle, post injection, which is now contaminated with the patient's blood and saliva. A single method dominates the dental field and it includes a two handed process. The syringe is normally held in the operator's favored hand and the needle cap is held in the other. The cap and needle are then slowly brought together, until the cap has sufficiently covered the needle and locked into place at the junction of the needle and syringe. If the needle misses the opening in the cap, there is a significant chance that the hand holding the cap will be stuck and the operator exposed to any blood-borne infection carried by the patient.

To avoid this problem, the Center for Disease Control currently recommends discarding disposable syringes without replacing the needle cap. However, this recommendation is impractical in the context of dental care. In dental care, requiring local anesthesia, the local anesthetic is administered at multiple locations within the patient's mouth, often over a time period, and frequently requiring repositioning of some combination of the patient, the patient's lips and/or tongue, or the dental caregiver. It is the widespread practice in the dental field to use a reusable syringe to administer all of the local anesthetic to the patient over these multiple uses. After treatment of the patient, the syringe is sterilized and reloaded with anesthetic agent, thus, in dental practice only the needle, the covers, and the anesthetic capsule (or cartridge) are disposable. When the syringe is used multiple times on a single patient to administer additional anesthetic, the dental care giver makes the practical calculation that reuse of the same syringe for treatment of a single patient saves time and money that outweighs the risk of an accidental stick by handling the uncapped syringe needle or when risking to recap the needle.

There are techniques for handling the recapping procedure to avoid the danger of a stick such as the "scooping" the cap off a table top, commonly called the 'one-handed scoop method' with the needle and pressing the cap against a wall to seat the cap on the needle base or holding the cap with a hemostat or forceps instead of the hand. These techniques work, but they are awkward at best, allow for the risk of picking up spatter, which might have fallen onto the dental tray and often ignored out of convenience. Moreover the method name is a misnomer; it in fact does require a second hand to fasten the cap securely to the needle hub once it is in place.

While this method is commonly taught in dental schools, it is rarely used by tenured dentists in favor of the two-handed technique.

Infanger, U.S. Pat. No. 9,682,196, entitled "Protective Cover for a Syringe Needle" discloses a protective cover, and is incorporated herein by reference in its entirety. Mohammed, U.S. Patent Application Publication No. 2006/0282044 entitled "Hypodermic Syringe Needle Assembly" and Harber et al. U.S. Pat. No. 5,405,326 entitled "Disposable Safety Syringe with Retractable Shuttle for Luer Lock Needle" also disclose safety syringe systems. However, each of those devices rely upon the user skill and experience to determine if the needle has been fully secured to the syringe. Under tightening of the needle and syringe negates the protective features of the cover, as the cover, needle, and/or syringe may become disconnected during use, exposing the patient or dental caregiver to prick risk. Particularly, in dental syringes, where the needle must be removed from the syringe after use, overtightening can require over-exertion to remove the protective cover and needle after use, which may cause a needle stick through device misoperation, breakage, or failure.

Accordingly, there is a clearly felt need in the art for a protective cover for a dental syringe needle, which reduces the risk of injury due to exposure to blood borne pathogens, because of accidental needle stick injuries incurred, while attempting to recap a syringe needle, and while securing and removing the safety needle from the dental syringe.

BRIEF DISCLOSURE

An exemplary embodiment of a protective dental needle includes a sheath that includes a cylindrical body. The cylindrical body includes a channel oriented along a length dimension along with cylindrical body. A needle assembly includes a hypodermic needle that extends through a hub. The needle assembly is retained within the sheath and is moveable within the sheath between a retracted position and an extended position. A needle cap is positioned external to the sheath. The needle cap includes a plurality of longitudinal ribs that extend from an interior surface of the needle cap.

In a further exemplary embodiment of the protective dental needle, a hub cap engages the needle cap to form a protective capsule about the sheath and the needle assembly. The needle cap may engage the sheath with a friction fit between the longitudinal ribs and the cylindrical body. The needle cap may be rotatable relative to the sheath about a common axis of the sheath and the needle cap. The cylindrical body may include at least two channels oriented along the length dimension of the cylindrical body. Rotation of the needle cap relative to the sheath is successively moved each longitudinal rib of the plurality of longitudinal ribs into and then out of a channel of the at least two channels of the cylindrical body. Movement of the longitudinal ribs into and then out of the at least two channels produces an audible sound.

Exemplary embodiments of the protective dental needle may further include a needle obstruction that extends from the interior surface of the needle cap along a common axis of the needle assembly, the sheath and the needle cap. The needle obstruction may engage a tip of the hypodermic needle. The sheath may include an end with a needle opening and the needle cap may further include an annular sheath ridge that extends from the interior surface of the needle cap and is configured to engage the end of the sheath around the needle opening.

In still further exemplary embodiments of the protective dental needle, a retention slot extends through the cylindrical body and is oriented perpendicular to the channel. The hub may include a lock tab that extends through the cylindrical body and is translatable within the channel and a retractive lock slot to move the needle assembly between the extended position and the retracted position. The retention slot may be located at a syringe end of the channel. A lock slot may be arranged perpendicular to the channel and arranged opposite the retractive lock slot across the channel. The retention slot may include at least one lock projection that extends into the retention slot and resiliently engages at least one lock element of the lock tab to resiliently retain the lock tab within the retention slot. The lock slot may include at least one lock projection that extends into the lock slot and causes deformation of at least one lock element as the lock tab moves from the channel into the lock slot and engages the at least one lock element to obstruct movement of the lock tab into the channel from the lock slot.

An exemplary embodiment of a method of limiting dental needle pricks includes providing a protective dental needle that includes a sheath with a cylindrical body and a channel oriented along a length dimension of the cylindrical body. A needle assembly includes a hypodermic needle that extends through a hub and is retained within the sheath and moveable within the sheath between a retracted position and an extended position. A needle cap is positioned external to the sheath and surrounds an injection end of the sheath and the needle assembly. The needle cap leave a syringe end of the sheath exposed. The need cap includes a plurality of longitudinal ribs that extend from an interior surface of the needle cap. A syringe is inserted into the syringe end of the sheath. The needle cap is rotated to secure the syringe to the needle assembly.

In additional exemplary embodiments of the method of limiting dental needle pricks, a hub cap is removed from engagement with a needle cap to expose the syringe end of the sheath. The needle cap may further include a need obstruction that extends from the interior surface of the needle cap along a common axis of the needle.

In still further exemplary embodiments of the method of limiting dental needle pricks, the plurality of longitudinal ribs engage an exterior surface of the cylindrical body to form a frictional connection between the needle cap and the cylindrical body. After the syringe is secured to the needle assembly, further rotation of the needle cap produces an audible sound as the longitudinal ribs move into and then out of the channel of the cylindrical body. The sheath may further include a retention slot that extends from the channel. The hub may include a lock tab that extends through the cylindrical body and is movable within the channel and the retention slot. The needle cap may be rotated to rotate the sheath relative to the needle assembly. The lock tab may engage the cylindrical lock body when the lock tab is positioned within the retention slot. Rotation of the need cap may rotate the sheath in the needle assembly relative to the syringe. After the syringe is secured to the needle assembly, further rotation of the needle cap may overcome the frictional connection between the needle cap and the cylindrical body and the needle cap may rotate relative to the syringe, the needle assembly, and the sheath.

DETAILED DISCLOSURE

Figure 1:
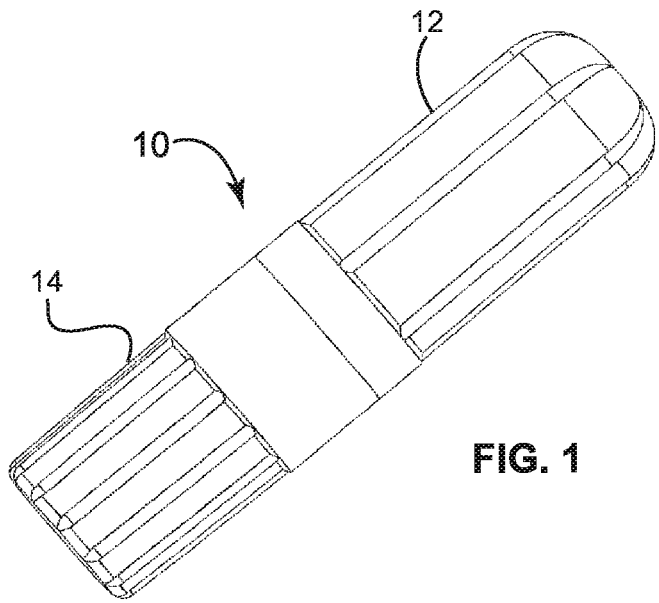
FIG. 1 depicts an exemplary embodiment of a capsule for a protective dental needle.

FIG. 1 depicts an exemplary embodiment of a capsule 10 that surrounds and encloses a protective dental needle as will be described in further detail herein. The capsule 10 is exemplarily formed in two parts with a needle cap 12 that surrounds an injection side of a protective dental needle and a hub cap 14 that surrounds a syringe side of the protective dental needle. The needle cap 12 and the hub cap 14 are resiliently secured together, for example by way of a friction or interference fit between the needle cap 12 and the hub cap 14. The interference fit between the needle cap 12 and the hub cap 14 creates a barrier to the environment out side of the capsule 10 about the protective dental needle. This maintains the protective dental needle in a sterile condition in which the protective dental needle is manufactured.

Figure 2:
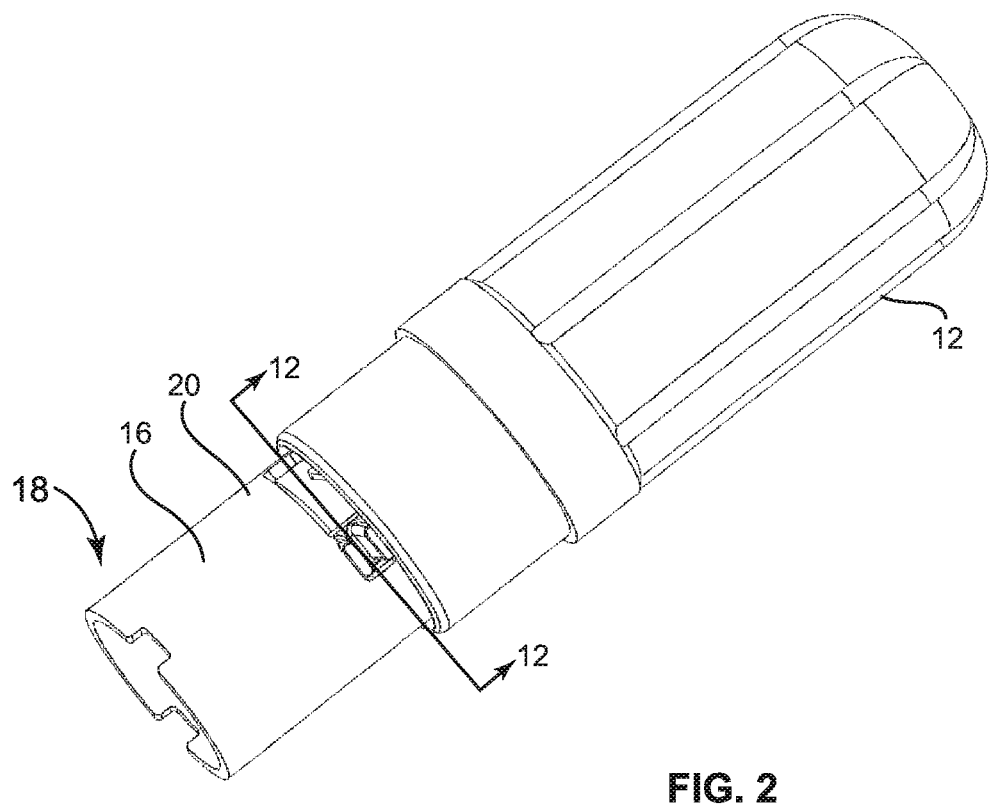
FIG. 2 depicts the capsule of FIG. 1 with the hub cap of the capsule removed to partially expose a sheath of the protective dental needle.

FIG. 2 provides the same image as FIG. 1, but with the hub cap 14 removed to expose a portion of the protective dental needle 16. Specifically, removal of the hub cap 14 exposes a syringe side 18 of the protective dental needle 16. As shown in FIG. 2, the protective dental needle 16 includes a sheath 20 which will be described in further detail herein, and is exemplarily provided in the form of a cylinder. Specifically, embodiments of the sheath 20 include a cylindrical body which had a major lengthwise axis along a longitudinal dimension of the protective dental needle 16.

Figure 3:
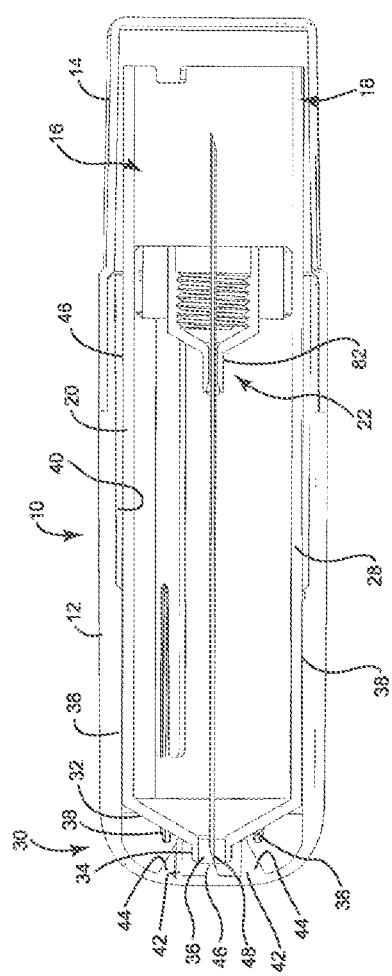
FIG. 3 is a cross-sectional view of a capsule surrounding a protective dental needle.
Figure 4:
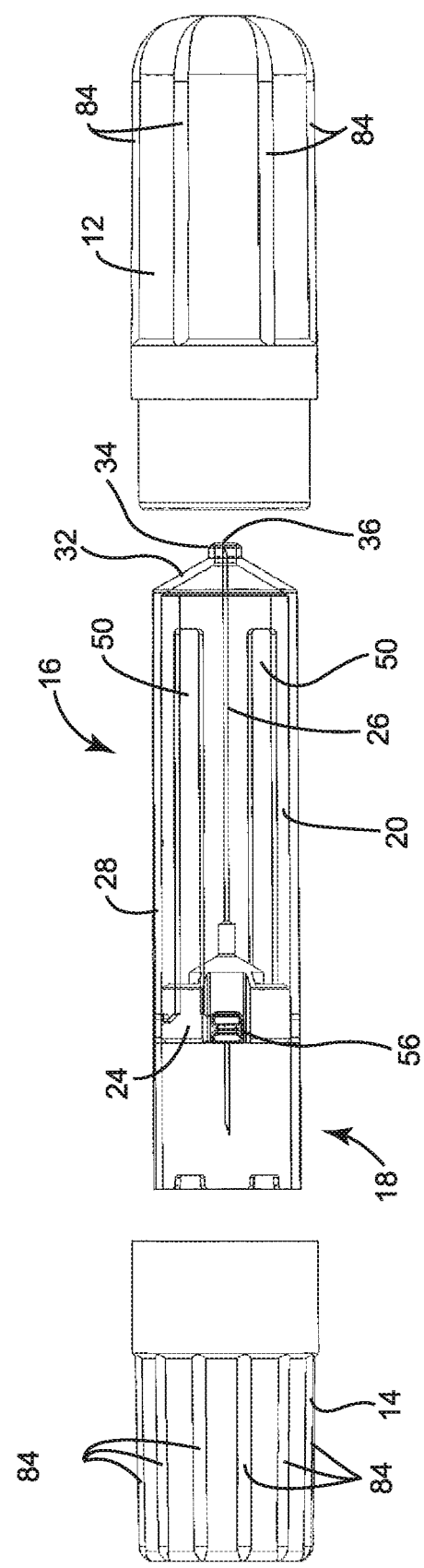
FIG. 4 is an exploded view of the protective dental needle and the capsule.

FIG. 3 is a cross-sectional view of the capsule 10 enclosed about the protective dental needle 16. FIG. 4 is an exploded view of the needle cap 12 and the hub cap 14 arranged relative to the protective dental needle 16. By way of reference to FIGS. 3 and 4, the protective dental needle 16 includes the sheath 20 which surrounds a needle assembly 22. The needle assembly 22, which will be described in further detail herein, exemplarily includes a hub 24 and a hypodermic needle 26 which extends through the hub 24, extending from both sides of the hub 24.

The sheath 20 is exemplarily formed of a cylindrical body 28 and a syringe side 18 of the sheath 20 extends beyond an end of the hypodermic needle 26. The syringe side 18 of the needle thus remains enclosed with the sheath 20 whether the needle assembly 22 is in a retracted position or an extended position. An injection side 30 of the sheath 20 terminates in an end 32 that is exemplarily in the shape of a cone or frustum. The end 32 terminates in a needle guide 34 which is exemplarily cylindrical in shape and includes a needle opening 36. As best seen in FIG. 3, the hypodermic needle 26 is axially aligned within the needle guide 34 through the needle opening 36. The needle assembly 22, sheath 20, hub cap 14, and needle cap 12 thus all have a common central axis about which these structures are aligned.

Further referring to FIG. 3, the friction or interference fit between the needle cap 12 and the hub cap 18 of the capsule 10 can be seen with a portion of the needle cap 12 being received within a receiving portion of the hub cap 14. It will be recognized that other arrangements of friction or interference fits between the needle cap 12 and the hub cap 14 may be used, and that other configurations of the capsule 10 may also be recognized by a person of ordinary skill in the art based upon the present disclosure, and particularly other arrangements of the hub cap 14 may be used apart from the embodiment as shown in the figures.

The needle cap 12 further includes a plurality of longitudinal ribs 38 that extend radially inwards from an interior surface 40 of the needle cap 12. The needle cap 12 further includes a sheath ridge 42 that is exemplarily an annular ridge that extends into the interior of the needle cap 12 from the interior surface 40 of the needle cap 12 at the injection side 30 of the needle cap 12. The sheath ridge 42 is exemplarily arranged coaxially to the cylindrical body 28 and the needle guide 34. The sheath ridge 42 extends a distance into the interior of the needle cap 12 such as to engage the end 32 of the sheath 20 when the needle cap 12 is secured about the protective dental needle 16. A series of support fins 44 may exemplarily extend from the sheath ridge 42 to the interior surface 40 of the needle cap 12 in order to provide additional rigidity to the sheath ridge 42.

In use, the ribs 38 engage an exterior surface 45 of the cylindrical body 28 of the sheath 20 and maintain the protective dental needle 16 axially oriented within the needle cap 12 and also resiliently retain the protective dental needle 16 within the needle cap 12 due to engagement between the ribs 38 and the sheath 20. The sheath ridge 42 further provides a point of engagement between the end 32 of the sheath 20 and maintains the injection side of the protective dental needle 16 axially or aligned within the needle cap 12. The needle cap 12 further includes a needle obstruction 46 which extends inwardly into the interior of the needle cap 12 from the interior surface 40 of the injection side end of the needle cap. The needle obstruction 46 is positioned in axial alignment with the hypodermic needle 26 when the protective dental needle 16 is retained within the needle cap 12. The needle obstruction 46 exemplarily extends into engagement with a tip 48 of the hypodermic needle 26 or into near-engagement with the tip 48. In one exemplary embodiment, the needle obstruction 46 terminates prior to or even with a plane formed by the end of the needle guide 34, while in other embodiments, the needle obstruction 46 may be dimensioned such that when the sheath ridge 42 engages the end 32 of the sheath 20, the needle obstruction 46 extends into the needle opening 36 beyond such a plane as defined by the end of the needle guide 34.

In exemplary embodiments as described in further detail herein, the dental caregiver may handle and manipulate the needle cap 12 during the use of the protective dental needle 16 as described in further detail herein. The needle obstruction 46, particularly in an arrangement which provides a localized mass of obstruction material relative to the tip 48 of the hypodermic needle 26 that resists puncture of the needle cap 12 by the hypodermic needle 26 during connection and removal of the protective dental needle 16 with a dental syringe.

Figure 5:
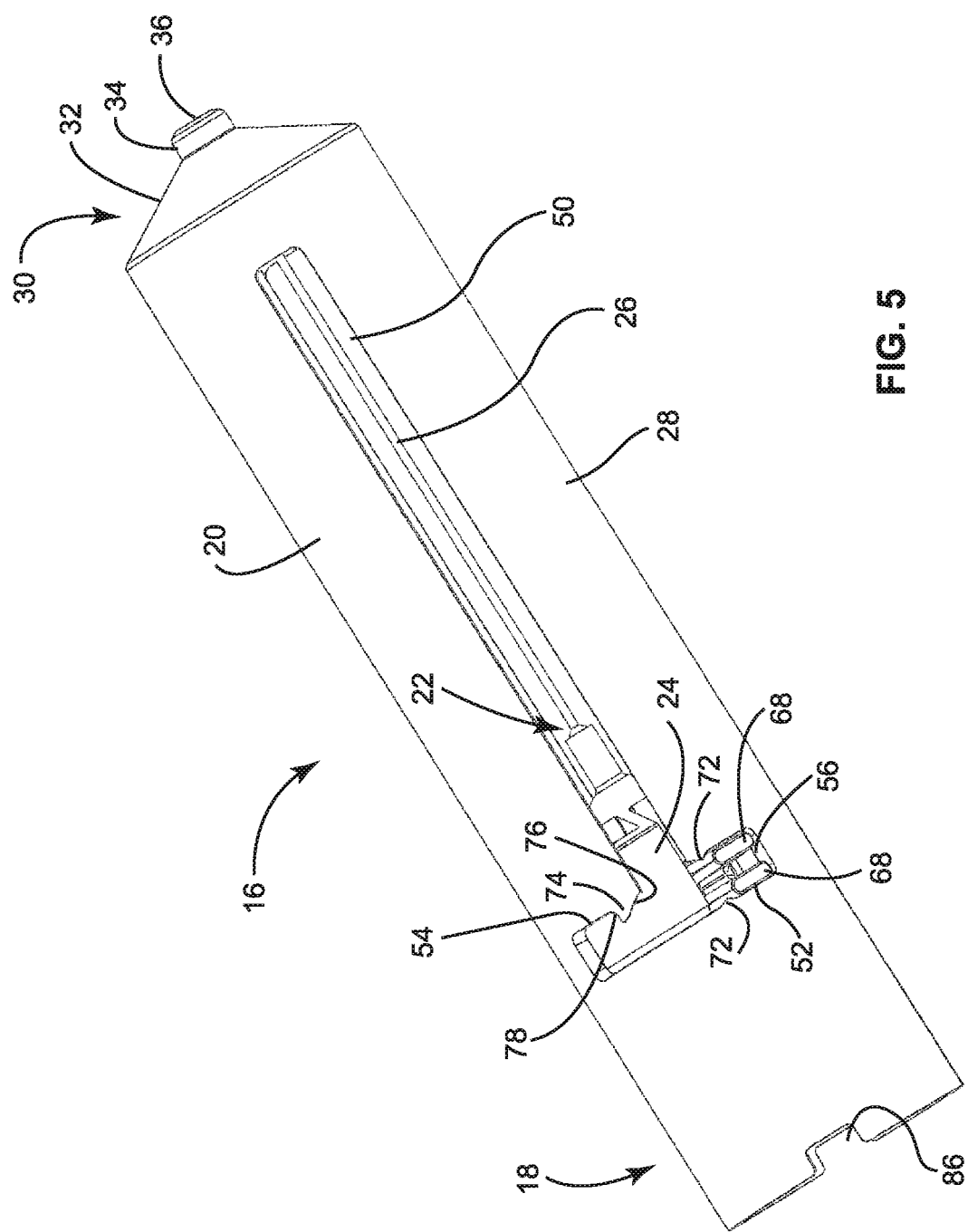
FIG. 5 is a perspective view of the protective dental needle in a retracted position.
Figure 6:
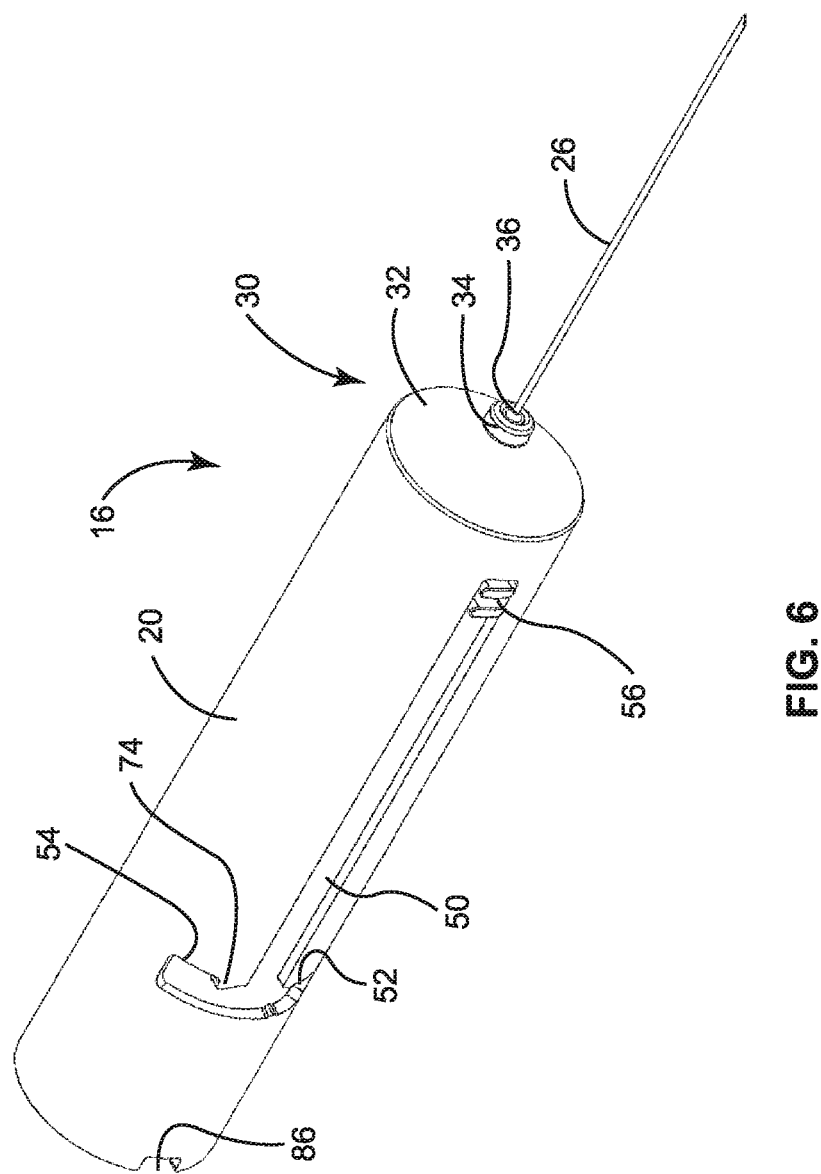
FIG. 6 is a perspective view of a protective dental needle in an extended position.

FIG. 5 depicts the protective dental needle 16 in a retracted position. FIG. 6 depicts the protective dental needle 16 in an extended position. The sheath 20 includes channels 50 that extend lengthwise along the sheath 20. Two lock slots are provided at the syringe side 18 of the channel 50. A retention slot 52 extends perpendicularly away from the channel 50 at the syringe side 18 end of the channel 50. Opposed from the retention slot 52 is a lock slot 54. The lock slot 54 is also oriented perpendicularly to the channel 50. In use, the sheath 20 and the needle assembly 22 located therein rotate and translate with respect to one another to move the protective dental needle 16 from the retracted position depicted in FIG. 5 to the extended position depicted in FIG. 6. In the retracted position, the needle assembly 22 is contained within the sheath 20 and a lock tab 56 that extends radially outward from the hub 24 is positioned within the retention slot 52. In the extended position depicted in FIG. 6, the lock tab 56 of the hub 24 is positioned at the injection side 30 of the channel 50 and the hypodermic needle 26 extends out of the needle guide 34 through the needle opening 36. When in the extended position, the needle neck 82 extends into the opening 36 of the needle guide 34. This centers the needle 26 within the sheath 20 in the extended position. Friction between the needle neck 82 and the needle guide, further provide a reversible connection between the needle assembly 22 and the sheath 20 when in the extended position.

Figure 7:
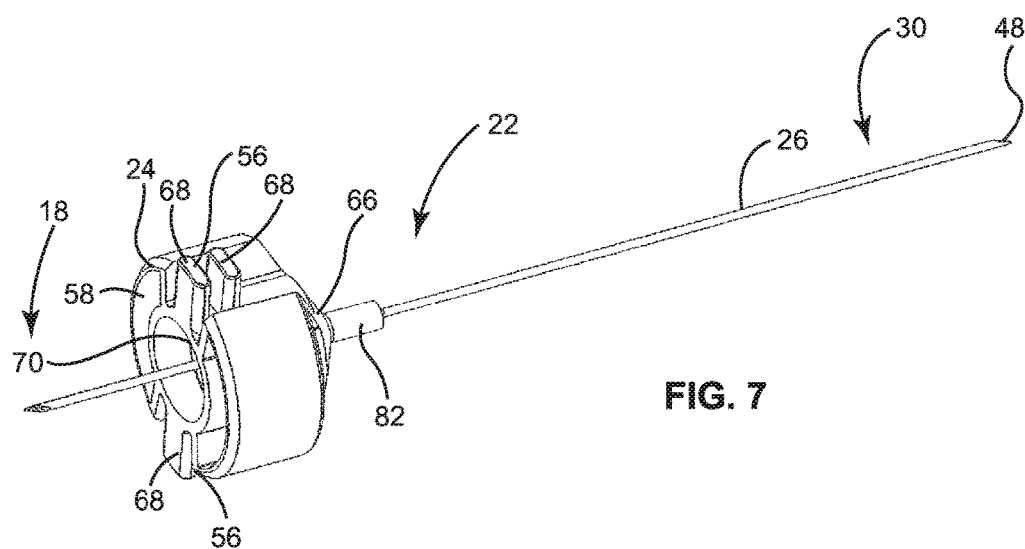
FIG. 7 is a perspective view of an exemplary embodiment of a needle assembly.
Figure 8:
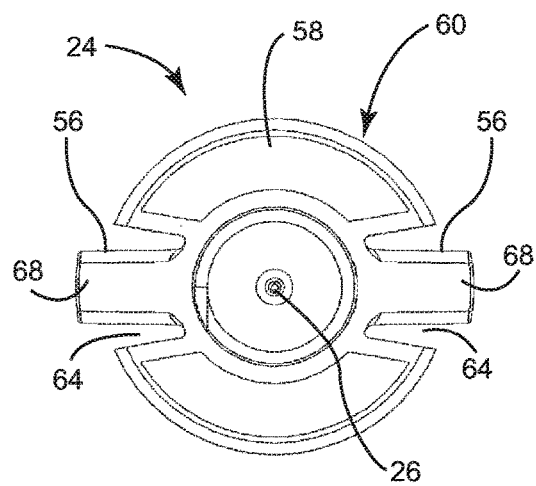
FIG. 8 is a front view of a needle assembly.
Figure 9:
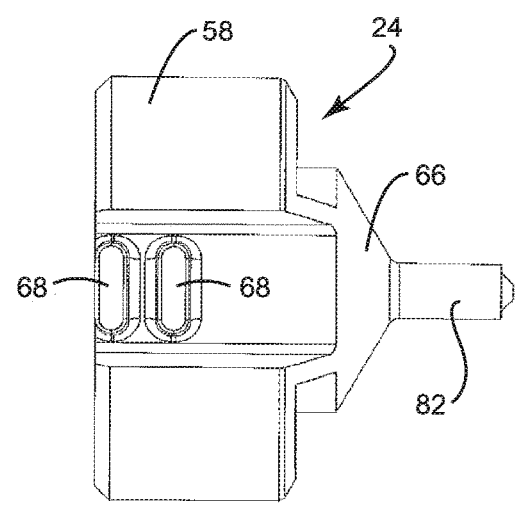
FIG. 9 is a side view of an exemplary embodiment of a hub.
Figure 10:
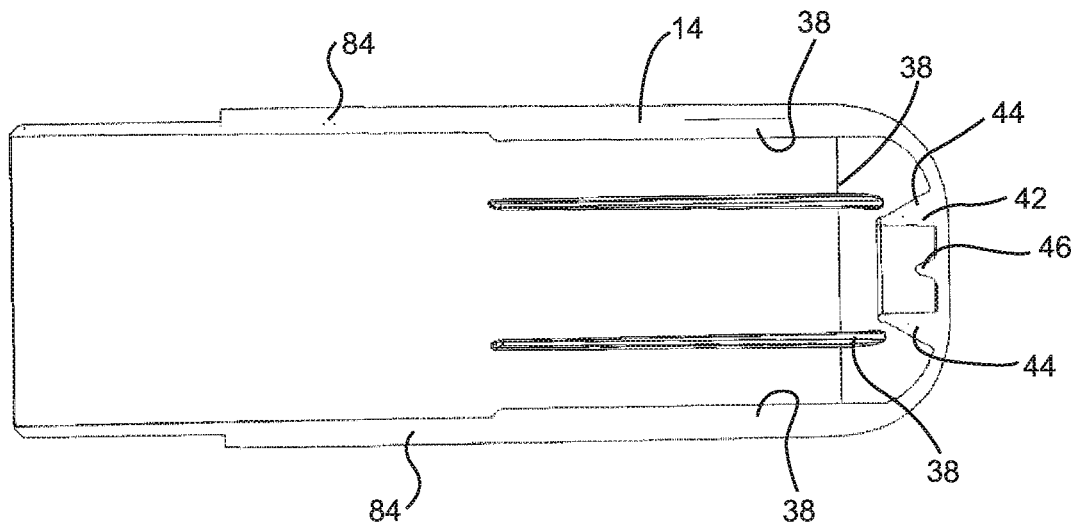
FIG. 10 is a cross-sectional view of an exemplary embodiment of a needle cap.
Figure 11:
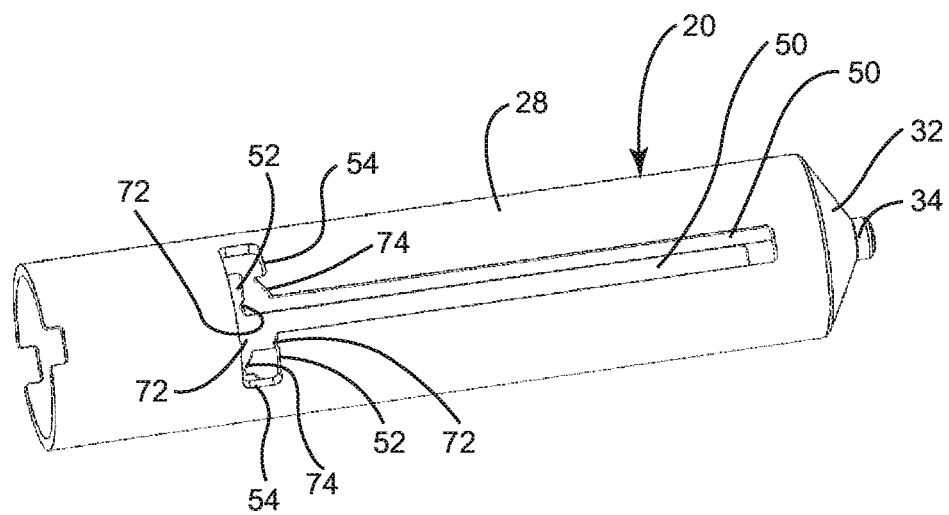
FIG. 11 is a perspective view of a sheath.

FIGS. 7 and 8 depict an exemplary embodiment of a needle assembly 22, while FIG. 9 presents a side view of an exemplary embodiment of a hub 24. The hub 24 includes a hub body 58. The hypodermic needle 26 is retained within the hub 24 to form the needle assembly 22. The hypodermic needle 26 extends past both ends of the hub 24. A needle neck 82 extends from the hub 24 along a portion of the hypodermic needle 26. The hub body 58 defines and outer perimeter 60. Lock tabs 56 extend radially outward from the hub body 58 exemplarily at opposite directions and orientations from one another relative to the axis provided by the hypodermic needle 26. In the embodiment depicted, the hub body 58 defines two opposing grooves 64 and the respective lock tabs 56 extend outward from within the grooves 64. The hub body 58 further comprises a conical face 66 that angles in an apex towards the axis provided by the hypodermic needle 26.

As shown in embodiments herein, the respective lock tabs 56 include two lock elements 68. The lock elements are exemplarily oriented parallel to each other with a major axis that is oriented perpendicularly relative to the hypodermic needle 26. The lock elements 68 are further arranged such as to be resiliently flexible and therefore flexible in a direction towards one another as will be described in further detail herein. The outer perimeter 60 of the hub body 58 is dimensioned such as to be slidable within the interior of the sheath 20. A threaded tap 70 is provided in the end of the hub 24 opposite the conical face 66. The hypodermic needle extends through the conical face 66 and through the hub body 58 and is oriented axially to the threaded tap 70. The hypodermic needle 26 thus extends beyond the hub 24 both to a syringe side 18 and to an injection side 30 of the hub 24.

Referring back to FIGS. 5 and 6, the needle assembly 22 is positioned interior of the sheath 20 and the lock tab 56 extends beyond the outer perimeter 60 of the hub body 58 and through the openings provided by the channels 50, the retention slots 52 and the lock slots 54. Just as the hub 24 as depicted in the Figures includes two opposed lock tabs 56, it will be recognized that embodiments of the sheath 20 include two opposed combinations of channels 50, retention slots 52, and lock slots 54, such as to respectively receive a pair of the lock tabs 56 of the hub 24 as described herein. It will be recognized that other combinations of numbers of lock tabs 56, channels 50, retention slots 52, and lock slots 54, including, but not limited to one, three, or four sets thereof may be used in other embodiments of the protective dental needle 16. The sheath 20 further includes notches 86 in the syringe end 18. These notches 86 are used to receive the lock tabs 56 during assembly of the protective dental needle 16. With the lock tabs 56 aligned, the needle assembly 22 can be translated into the sheath 20 and further into the channels 50.

As previously noted, in the retracted position, the needle assembly 22 is arranged with the lock tabs 56 positioned within the retention slots 52. The retention slots 52 exemplarily include at least one retention projection 72 extending from the cylindrical body 28 of the sheath 20 into the retention slot 52. In an exemplary embodiment, two retention projections 72 extend into the retention slot 52, for example, from opposed sides of the retention slot 52. In an exemplary embodiment, the retention projections 72 extend into the retention slot 52 a distance that is smaller than the minor dimension of the lock element 68. In still further exemplary embodiments, the retention projections 72 extend less than half of the minor dimension of the lock element 68. In exemplary embodiments, engagement between the lock elements 68 and the retention projections 72 inwardly deform the lock element 68 toward one another such that the lock tab 56 can be moved into the retention slot 52 past the retention projection 72. The retention projections 72 resiliently retain the lock tab 56 within the retention slot 52. In exemplary embodiments, the lock elements 68 are further dimensioned such as to also resiliently engage the sides of the retention slot 52 to further maintain the lock element 68 retention within the retention slot 52. This engagement thus requires a positive rotative force to be applied between the sheath 20 and the needle assembly 22. Rotation of these components relative to one another moves the lock tab 56 past the retention projection 72, including deformation of the lock elements 68 inwards towards each other. Once the lock tab 56 is in the channel 50, the needle assembly 22 and the sheath 20 can be translated relative to one another in order to position the lock tab 56 at the injection side 30 end of the channel 50. Movement of the needle assembly 22 to this position extends the hypodermic needle 26 out of the needle opening 36 in the needle guide 34. The dental caregiver can repeatedly translate the needle assembly 22 and sheath 20 relative to one another to move the protective dental needle 16 back into the retracted position and to move the lock tab 56 into the retention slot 52, the dental caregiver can repeat this process of moving the protective dental needle 16 between the extended and retracted positions as needed while treating a patient. When the dental caregiver is finished or the supply of anesthetic agent in the syringe is depleted, the dental caregiver moves the protective dental needle 16 into the retracted position but rotates the sheath 20 and the needle assembly 22 relative to one another to instead move the lock tab 56 into the lock slot 54.

The lock slot 54 includes a lock projection 74 that extends into the lock slot 54 from the cylindrical body 28 of the sheath 20. In an exemplary embodiment, the lock projection 74 includes a ramped surface 76 and an engagement surface 78. The engagement surface 78 is exemplarily perpendicular to the orientation of the lock slot 54. Additionally, the lock projection 74 is dimensioned to be greater than that of the retention projections 72 and in an embodiment, be dimensioned to be greater than half the minor dimension of the lock elements 68. In a further embodiment the lock projection extends a width of a minor dimension of the lock element 68. As previously noted, the lock elements 68 are deflectable such that engagement between the ramped surface 76 and the lock elements 68 inwardly deflects the lock elements 68 to move the lock elements 68 past the permanent lock protection 74 while once the lock tab 56 is positioned within the lock slot 54, the lock element 68 is blocked from movement by the engagement surface 78. Without the ramped surface 76 to facilitate deflection of the lock element 68, the lock elements 68 are retained within the lock slot 54 in a condition that is unchangeable without destruction or impairment of the device. While the exemplary embodiment depicts a single lock projection 74, it will be recognized that other embodiments include a second lock projection 74 that extends into the lock slot 54 from a side of the lock slot 54 opposite the lock projection 74 depicted in the Figures.

As previously noted, embodiments of the protective dental needle 16 as disclosed herein provide advantages over previous covered needles in that protected dental needed is particularly suited for use in securing to and being removed from a reusable syringe. Since in the dental practice, reusable syringes are used with a disposable needle, the initial connection of the disposable needle to the syringe raises a high risk of needle pricks. The safety of use of a disposable needle is further compromised when the disposable needle is secured too loosely or too tightly to the reusable syringe. If the disposable needle is secured too loosely, the disposable needle can disconnect from the reusable syringe during treatment of the patient. If the disposable needle is secured too tightly then the dental caregiver must exert and outsized level of force to disconnect the disposable needle from the reusable syringe, which increases the possibility of breakage of the disposable needle which may result in harm to the dental care giver. Features of the needle cap 12 and interaction thereof with the sheath 20 present a solution to the aforementioned problems.

When the dental caregiver obtains a new protective dental needle for use in treating a patient, the protective dental needle 16 comes enclosed in a needle capsule 10 as depicted in FIG. 1. The dental caregiver removes the hub cap 14 from the needle cap 12, exposing the syringe side 18 of the protective dental needle 16. It will be recognized that the friction fit exemplarily as provided by engagement between the longitudinal ribs 38 on the interior of the needle cap 12, and the exterior of the sheath 20 provides a greater coefficient of friction than the engagement between the hub cap 14 and the needle cap 12. In this manner, a separative force applied to the needle cap 12 and the hub cap 14 separates the hub cap 14 from the needle cap 12 without moving the protective dental needle 14 relative to the needle cap 12. The needle cap 12 and the hub cap 14 may further include external ribs 84 that facilitate user grip of the exterior of the capsule.

With the protective dental needle 16 as shown in FIG. 2, the dental caregiver inserts a syringe into the syringe side 18 of the sheath 20. The dental caregiver brings a threaded end of the syringe into engagement with the threaded tap 70 of the needle assembly 22. The dental caregiver can grip the syringe with one hand and the needle cap 12 with the other hand. This grip and the applied rotative force as described herein provided by the dental caregiver is helped by the external ribs 84 of the needle cap 12. The protective dental needle 16 is first provided with the lock tabs 56 positioned within the lock slots 54. When the needle assembly 22 is positively in contact on the end of the syringe, the threaded tap 70 can begin to be fitted to the end of the syringe. As the threads of the threaded tap 70 and the end of the syringe engage, the lock tabs 56 move from the lock slots 54 and into the retention slots 52, this provides audible and tactile clicks as the tabs 56 move past lock projections 74, retention projections 72 and into engagement with the sheath 20. This gives the dental caregiver a first indication that the connection between the syringe and the protective dental needle 16 is progressing. As depicted in FIG. 3, the dental caregiver's hand is protected from an inadvertent needle stick by the needle cap 12 since the needle obstruction 46 provides an outsized barrier to puncture from the needle 26 should the lock tab 56 inadvertently move into the channel 50 and pressure applied by the dental caregiver to the syringe place an extending force on the needle assembly 22.

Figure 12:
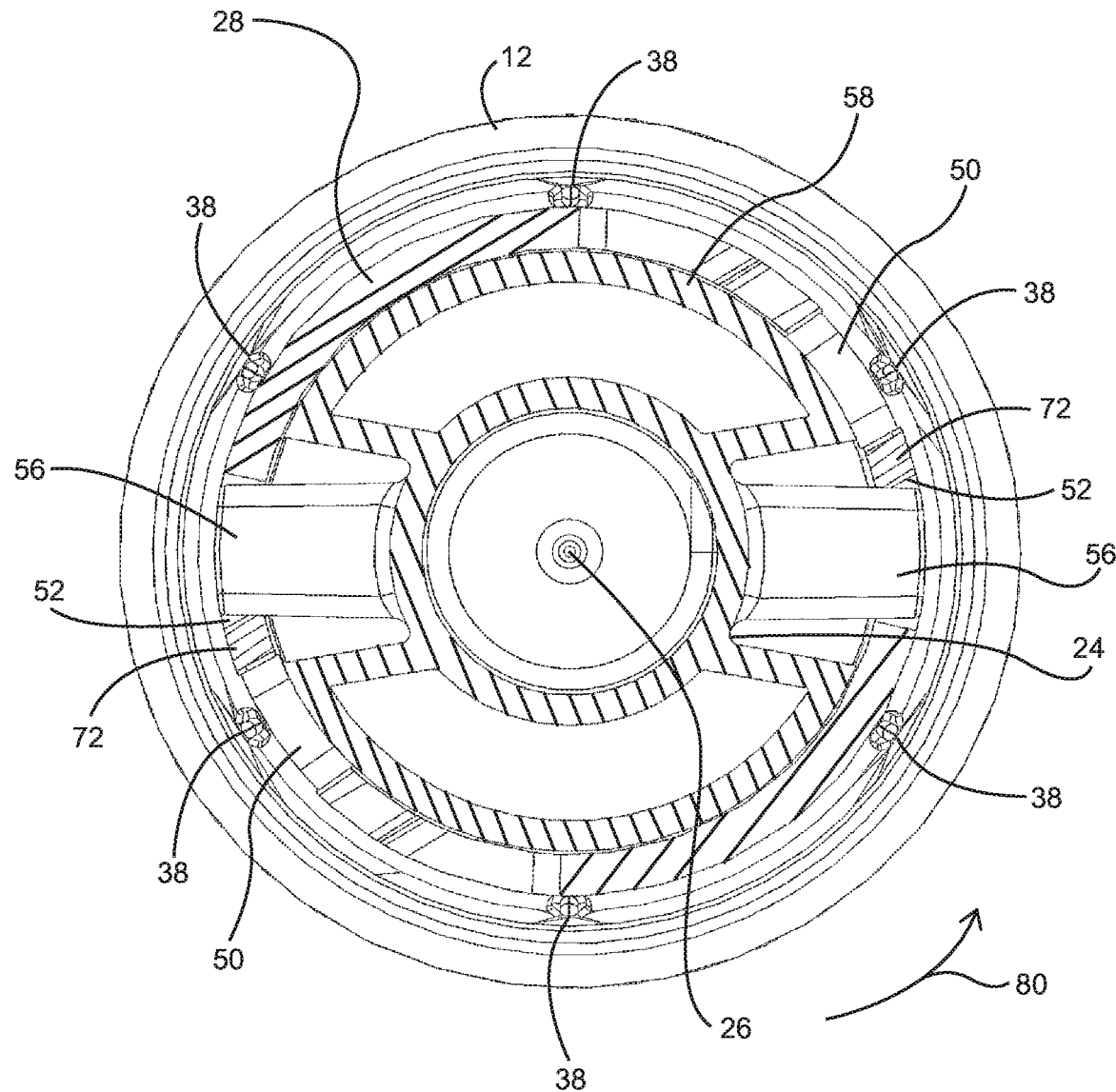
FIG. 12 is a cross-sectional view taken along line 12-12 of FIG. 2.

Referring now to FIG. 12, FIG. 12 is a cross sectional view as taken along line 12-12 of FIG. 2. To secure the reusable syringe to the protective dental needle 16, the dental caregiver exemplarily rotates the needle cap 12 in a counterclockwise direction as exemplified by arrow 80 in FIG. 12. The external ribs 84 of the needle cap 12 facilitate grip of the dental caregiver to rotate the needle cap 12. The interior of the needle cap 12 includes a plurality of spaced apart longitudinal ribs 38. The friction fit between the longitudinal ribs 38 and the sheath 20 will generally cause the rotative force applied to the needle cap 12 to be translated to the sheath 20. This will rotate the needle cap 12 and the sheath 20 relative to the needle assembly 22 and hub 24. If the lock tabs 56 are not already secured within the retention slots 52, such rotation will move the sheath 20 relative to the hub 24 positioning the lock tabs 56 within the retention slots 52. It will be recognized that the frictional connection between the needle cap 12 and the sheath 20 is exemplarily greater than a frictional resistance provided by the retention projection 72 on the lock element 68 of the lock tabs 56 and therefore the needle cap 12 and the sheath 20 will remain in engagement while the lock tabs 56 are moved relative past the retention projections 72 into the retention slot 52. Once in the retention slot 52, the sheath 20 engages the lock tabs 56 and the counterclockwise rotative force applied to the needle cap 12 is similarly transferred to the needle assembly 52. This moves the needle assembly 22 and the threaded tap 70 thereof relative to the syringe threadingly connecting the reusable syringe to the protective dental needle 16.

However, once the reusable syringe is fully threaded onto the protective dental needle 16, the resistance of the threaded tap 70 of the needle assembly 22 against the reusable syringe is greater than the frictional resistance between the longitudinal ribs 38 of the needle cap 12 and the sheath 20. The needle cap 12 will thus continue to rotate in the direction of arrow 80 relative to the sheath 20 and the longitudinal ribs 38 will progressively drop into and out of the channels 50 within the sheath 20. Each of these actions will come with an audible click between the surfaces of the needle cap 12 and the sheath 20. The dental caregiver will thus be provided with a series of audible clicks to notify the dental caregiver that the protective dental needle 16 is fully secured to the reusable syringe. This sliding movement of the needle cap 12 relative to the sheath 20 further limits the force that the dental care giver can place on the threaded junction between the protective dental needle and the reusable syringe. Therefore, the slipping of the needle cap 12 relative to the sheath 20 prevents overtightening of the protective dental needle onto the reusable syringe.

After this, the protective dental needle 16 is secured to the reusable syringe. The needle cap 12 can be pulled axially from the sheath 20 the needle cap 12 can be disposed of at this time as it is not required for intra use protection of the hypodermic needle 26. The sheath 20 encloses the hypodermic needle 26 is the protective dental needle 16 in the retracted position with the hypodermic needle 26 within the sheath 20.

The dental caregiver repeatedly operates the protective dental needle 16 between the retracted and extended positions to provide the local anesthesia treatment to the patent as needed. When the protective dental needle 16 is to be removed from the reusable syringe, the protective dental needle 16 is moved to the retracted position. This time the dental caregiver rotates the sheath 20 and the syringe in the opposite direction to move the tabs 56 into the lock slots 54. With the tabs 56 secured in the lock slots an axially rotative force on the sheath 20 in a clockwise direction is translated to the needle assembly 22 by interaction of the cylindrical body 28 on the tab 56. In an embodiment, the dental caregiver can replace the needle cap 12 about the sheath 20 to improve grip to rotate the protective dental needle 16 relative to the syringe. Additionally, the needle cap 12 can provide further protection against needle sticks as described above. The rotative force between the protective dental needle 16 and the syringe unthreads the needle assembly 22 from the reusable syringe. This further helps to maintain the protective dental needle 16 in the permanently locked retracted position, providing protection against needle sticks as no force is applied between the element 68 and the permeant lock projection 74. Once removed, the needle assembly 22 is held entirely within the sheath 20 and may be disposed of according to normal medical practice and care.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A protective dental needle, comprising:
   a sheath comprising a cylindrical body with at least two channels oriented along a length dimension of the cylindrical body, the sheath extending from an open syringe end to an end with a needle opening;
   a needle assembly comprising a hypodermic needle extending through a hub, the needle assembly retained within the sheath and movable within the sheath between a retracted position and an extended position, wherein a portion of the hypodermic needle extends through the needle opening when the needle assembly is in the extended position;
   a needle cap positioned coaxially external to the sheath about the end with the needle opening, the needle cap having a plurality of longitudinal ribs extending from an interior surface of the needle cap to engage the sheath, wherein the needle cap engages the sheath with a friction fit between the longitudinal ribs of the needle cap and the cylindrical body of the sheath, and the needle cap is rotatable relative to the sheath about a common axis of the sheath and the needle cap; and
   a hub cap positioned coaxially external to the sheath about the open syringe end, wherein the hub cap and the needle cap engage to form a capsule about the sheath and the needle assembly;
   wherein rotation of the needle cap relative to the sheath successively moves each longitudinal rib of the plurality of longitudinal ribs into and then out of the at least two channels of the cylindrical body.

2. The protective dental needle of claim 1, wherein the needle assembly is free of the needle cap and the hub cap, and engagement of the plurality of longitudinal ribs of the needle cap with the sheath configure the needle cap, the sheath, and the needle assembly to rotate together.

3. The protective dental needle of claim 1, wherein movement of the longitudinal ribs into and then out of the at least two channels produces an audible sound.

4. The protective dental needle of claim 1, wherein the needle cap further comprises a needle obstruction that extends from the interior surface of the needle cap along a common axis of the needle assembly, the sheath, and the needle cap.

5. The protective dental needle of claim 4, wherein the needle obstruction engages a tip of the hypodermic needle.

6. The protective dental needle of claim 4, wherein the needle cap further comprises an annular sheath ridge that extends from the interior surface of the needle cap and is configured to engage the end of the sheath around the needle opening.

7. The protective dental needle of claim 1, further comprising a retention slot through the cylindrical body and oriented perpendicular to the at least two channels; and
   wherein the hub comprises a lock tab that extends through the cylindrical body and translatable within the at least two channels and the retention slot to move the needle assembly between the extended position and the retracted position.

8. The protective dental needle of claim 7, wherein the retention slot is located at a syringe end of the at least two channels.

9. The protective dental needle of claim 8, further comprising a lock slot arranged perpendicular to the at least two channels and arranged opposite the retention slot across the at least two channels.

10. The protective dental needle of claim 9, wherein the retention slot comprises at least one lock projection that extends into the retention slot and resiliently engages at least one lock element of the lock tab to resiliently retain the lock tab within the retention slot; and
    wherein the lock slot comprises at least one lock projection that extends into the lock slot and causes deformation of the at least one lock element of the lock tab as the lock tab moves from the at least two channels into the lock slot and the at least one lock projection engages the at least one lock element of the lock tab to obstruct movement of the lock tab into the at least two channels from the lock slot.

11. A method of limiting dental needle pricks, the method comprising:
    providing a protective dental needle comprising:
      a sheath comprising a cylindrical body with a channel oriented along a length dimension of the cylindrical body, the sheath extending from an open syringe end to an end with a needle opening;
      a needle assembly comprising a hypodermic needle extending through a hub, the needle assembly retained within the sheath and movable within the sheath between a retracted position and an extended position, wherein a portion of the hypodermic needle extends through the needle opening when the needle assembly is in the extended position;
      a needle cap positioned coaxially external to the sheath about the end with the needle opening, the needle cap surrounding an injection end of the sheath and the needle assembly and the needle cap leaves a syringe end of the sheath exposed, the needle cap having a plurality of longitudinal ribs extending from an interior surface of the needle cap to engage the sheath wherein the plurality of longitudinal ribs engage an exterior surface of the cylindrical body to form a frictional connection between the needle cap and the cylindrical body; and a hub cap positioned coaxially external to the sheath about the open syringe end, wherein the hub cap and needle cap engage to form a capsule about the sheath and the needle assembly;

removing the hub cap from engagement with the needle cap to expose the open syringe end of the sheath inserting a syringe into the open syringe end of the sheath; and rotating the needle cap relative to the syringe wherein engagement of the plurality of longitudinal ribs of the needle cap with the sheath imparts rotation from the needle cap to the needle assembly through the sheath to secure the syringe to the needle assembly;

wherein after the syringe is secured to the needle assembly further rotation of the needle cap produces an audible sound as the longitudinal ribs sequentially move into and then out of the channel of the cylindrical body.

12. The method of claim 11, wherein prior to removing the hub cap from engagement with the needle cap, the capsule creates a barrier to an environment outside of the capsule to hold the sheath and needle assembly in a sterile condition within the capsule.

13. The method of claim 11, wherein the needle cap further comprises a needle obstruction that extends from the interior surface of the needle cap along a common axis of the needle assembly, the sheath, and the needle cap to a position proximate a tip of the hypodermic needle.

14. A method of limiting dental needle pricks, the method comprising:
   providing a protective dental needle comprising:
      a sheath comprising a cylindrical body with a channel oriented along a length dimension of the cylindrical body, the sheath extending from an open syringe end to an end with a needle opening;
      a needle assembly comprising a hypodermic needle extending through a hub, the needle assembly retained within the sheath and movable within the sheath between a retracted position and an extended position, wherein a portion of the hypodermic needle extends through the needle opening when the needle assembly is in the extended position;
      a needle cap positioned coaxially external to the sheath about the end with the needle opening, the needle cap surrounding an injection end of the sheath and the needle assembly and the needle cap leaves a syringe end of the sheath exposed, the needle cap having a plurality of longitudinal ribs extending from an interior surface of the needle cap to engage the sheath wherein the plurality of longitudinal ribs engage an exterior surface of the cylindrical body to form a frictional connection between the needle cap and the cylindrical body; and a hub cap positioned coaxially external to the sheath about the open syringe end, wherein the hub cap and needle cap engage to form a capsule about the sheath and the needle assembly;

removing the hub cap from engagement with the needle cap to expose the open syringe end of the sheath inserting a syringe into the open syringe end of the sheath; and rotating the needle cap relative to the syringe wherein engagement of the plurality of longitudinal ribs of the needle cap with the sheath imparts rotation from the needle cap to the needle assembly through the sheath to secure the syringe to the needle assembly;

wherein the sheath further comprises a retention slot that extends from the channel and the hub comprises a lock tab that extends through the cylindrical body and is movable within the channel and the retention slot and the method further comprises:

rotating the needle cap to rotate the sheath relative to the needle assembly; and engaging the lock tab with the cylindrical body when the lock tab is positioned within the retention slot, then rotating the needle cap to rotate the sheath and the needle assembly relative to the syringe.

15. The method of claim 14, wherein after the syringe is secured to the needle assembly, further rotation of the needle cap overcomes the frictional connection between the needle cap and the cylindrical body and the needle cap rotates relative to the syringe, the needle assembly, and the sheath.

16. The method of claim 14, wherein prior to removing the hub cap from engagement with the needle cap, the capsule creates a barrier to an environment outside of the capsule to hold the sheath and needle assembly in a sterile condition within the capsule.

17. The method of claim 14, wherein the needle cap further comprises a needle obstruction that extends from the interior surface of the needle cap along a common axis of the needle assembly, the sheath, and the needle cap to a position proximate a tip of the hypodermic needle.

* * * * *